(12) United States Patent
Sonobe et al.

(10) Patent No.: US 8,309,130 B2
(45) Date of Patent: Nov. 13, 2012

(54) ADSORBENT FOR ORAL ADMINISTRATION

(75) Inventors: Naohiro Sonobe, Fukushima (JP);
Susumu Morimoto, Tokyo (JP);
Hideyuki Yoshihara, Tokyo (JP);
Hiroyuki Hanatsuka, Fukushima (JP);
Makoto Arakawa, Fukushima (JP)

(73) Assignee: Kureha Corporation, Tokyo (JP)

( * ) Notice: Subject to any disclaimer, the term of this patent is extended or adjusted under 35 U.S.C. 154(b) by 98 days.

(21) Appl. No.: 12/630,581

(22) Filed: Dec. 3, 2009

(65) Prior Publication Data
US 2010/0074954 A1 Mar. 25, 2010

Related U.S. Application Data

(60) Division of application No. 10/948,314, filed on Sep. 24, 2004, now Pat. No. 7,651,974, which is a continuation-in-part of application No. PCT/JP03/14011, filed on Oct. 31, 2003.

(30) Foreign Application Priority Data

Nov. 1, 2002 (JP) ................................ 2002-320254

(51) Int. Cl.
*A61K 9/18* (2006.01)
*A61K 33/44* (2006.01)
*A61P 1/16* (2006.01)
*A61P 31/12* (2006.01)
(52) U.S. Cl. ......... 424/484; 424/125; 502/418; 514/769
(58) Field of Classification Search .................. 502/416, 502/418; 514/769; 424/484, 125
See application file for complete search history.

(56) References Cited

U.S. PATENT DOCUMENTS 5,573,761 A * 11/1996 Ise et al. ........................ 424/125
(Continued)

FOREIGN PATENT DOCUMENTS
EP 29715 A1 6/1981
(Continued)

OTHER PUBLICATIONS

A. Gardziella et al.; Interceram; "Carbon From Phenolic Resins: Carbon Yield and Volatile Components—Recent Studies"; 1992; pp. 461-467; vol. 41, No. 7/8; Essen, Germany.

(Continued)

*Primary Examiner* — Daniel C. McCracken
(74) *Attorney, Agent, or Firm* — Sughrue Mion, PLLC

(57) ABSTRACT

An adsorbent for oral administration, characterized by comprising a spherical activated carbon, wherein a diameter is 0.01 to 1 mm, a specific surface area determined by Langmuir's adsorption equation is 1000 m$^2$/g or more, and a diffraction intensity ratio, an R value, determined by an equation (1):

$$R=(I_{15}-I_{35})/(I_{24}-I_{35}) \qquad (1)$$

wherein $I_{15}$ is a diffraction intensity when a diffraction angle (2θ) of an X-ray diffractometry is 15°, $I_{35}$ is a diffraction intensity when a diffraction angle (2θ) of an X-ray diffractometry is 35°, and $I_{24}$ is a diffraction intensity when a diffraction angle (2θ) of an X-ray diffractometry is 24°, is 1.4 or more; and an adsorbent for an oral administration, characterized by comprising a surface-modified spherical activated carbon, wherein a diameter is 0.01 to 1 mm, a specific surface area determined by Langmuir's adsorption equation is 1000 m$^2$/g or more, a total amount of acidic groups is 0.40 to 1.00 meq/g, a total amount of basic groups is 0.40 to 1.10 meq/g, and a diffraction intensity ratio, an R value, determined by equation (1) is 1.4 or more. The adsorbents for oral administration exhibit a useful selective adsorbability, that is, a less adsorbability of useful substances in a body, and a greater adsorbability of toxic substances.

14 Claims, 6 Drawing Sheets

U.S. PATENT DOCUMENTS

| | | | |
|---|---|---|---|
| 5,820,967 | A | 10/1998 | Gadkaree |
| 2005/0079167 | A1 | 4/2005 | Sonobe et al. |
| 2005/0112114 | A1 | 5/2005 | Sonobe et al. |

FOREIGN PATENT DOCUMENTS

| | | | |
|---|---|---|---|
| EP | 595715 | A1 | 5/1994 |
| EP | 0711561 | | 5/1996 |
| EP | 0711561 | A2 | 5/1996 |
| EP | 1249241 | A1 | 10/2002 |
| EP | 1 440 692 | A | 7/2004 |
| GB | 2 012 257 | A | 7/1979 |
| GB | 2 053 176 | A | 2/1981 |
| GB | 2 280 898 | A | 2/1995 |
| JP | 54-089010 | | 7/1979 |
| JP | 56-005313 | | 1/1981 |
| JP | 56-28766 | | 3/1981 |
| JP | 56-028766 | A | 3/1981 |
| JP | 57-136455 | A | 8/1982 |
| JP | 58-213613 | A | 12/1983 |
| JP | 59-006208 | | 1/1984 |
| JP | 63-051161 | | 10/1988 |
| JP | 64-056141 | | 3/1989 |
| JP | 04-338107 | | 11/1992 |
| JP | 6211611 | | 8/1994 |
| JP | 07-165407 | | 6/1995 |
| JP | 08-040918 | | 2/1996 |
| JP | 08-208491 | | 8/1996 |
| JP | 10-316578 | | 12/1998 |
| JP | 11-001314 | | 1/1999 |
| JP | 11-029485 | | 2/1999 |
| JP | 11-049503 | | 2/1999 |
| JP | 11-060664 | | 3/1999 |
| JP | 11-116648 | | 4/1999 |
| JP | 11-217278 | | 8/1999 |
| JP | 11-292770 | A | 10/1999 |
| JP | 11-292771 | A | 10/1999 |
| JP | 2000-233916 | | 8/2000 |
| JP | 2001-114852 | | 4/2001 |
| JP | 2001-288238 | | 10/2001 |
| JP | 2004-244414 | | 9/2004 |
| SU | 1836138 | A3 | 8/1993 |
| WO | 2004/039380 | A1 | 5/2004 |

OTHER PUBLICATIONS

Hiroshi Kitagawa et al.; Steam Activation of Phenolformaldehyde Resin; Japanese Journal; Kogyo-Kagaju-Zasshi; Journal of Chemistry; vol. 73, No. No; pp. 38-42, 1970.

A. Gardziell et al.; Carbon from Phenolic Resins; Carbon Yield and Voatile Components-Reent Studies; pp. 22-26; 1992.

Yang et al, Preparation and Properties of Phenolic Resin-Based Activated Carbon Spheres With Controlled Pore Size Distribution, Carbon, May 2002, pp. 911-916, vol. 40—No. 6. (XP004346745).

Hard Activated Carbon As Adsorbent in Blood Filtration, Chemical Abstracts + Indexes, American Chemical Society, 1982, pp. 394, vol. 97—No. 22. (XP002314268).

Activated Carbon for Artificial Kidney, Chemical Abstracts + Indexes, American Chemical Society, 1981, pp. 384, vol. 94—No. 22. (XP002314269).

Hiroshi Kitagawa, "Preparation of Active Carbon from Phenolformaldehyde Resin", a Japanese Journal "NihonKagaku-Kaishi", No. 6, pp. 1144-1150, 1972.

Yutaka Fukumoto, et al., "Production of Activated Carbon from Waste Phenol Resin", a Japanese Journal "TANSO" (Carbon), No. 188, pp. 138-142, 1999.

Shigeaki Kasaoka, at al., "Preparation of Activated Fibrous Carbon from Phenolic Fabric and Its Molecular Sieving Properties", a Japanese Journal "Nihon-KagakuKaishi" (A Chemical Society of Japan), No. 6, pp. 9901000, 1987.

Eiichi Asada, et al., a Japanese Text Book "X-sen Bunseki: Kiso-Bunseki-Kagaku Koza, No. 24" (X-ray Analysis: Basic Course of Analytical Chemistry), published by Kyoritsu Shuppan Co., Ltd., pp. 52-53, 1968.

"Saishin-no-Tanso-Zairyo Jikken Gijutsu: Bunseki, Kaiseki-Hen" a Japanese Text Book (Latest Experimental Technique of Carbon Substance), edited by Carbon Society of Japan, pp. 156-161, 2001.

"Activated carbon", a Japanese Dictionary "Eagaku-jiten" (Chemical dictionary), Oct. 2, 2000, Tokyo Kagaku Dozin Co., Ltd.

Experiment Report, "Influences of measuring and analyzing conditions on R values", Jul. 13, 2007, by Japan EnviroChemicals Co., Ltd.

"Hyperuricemia", at al., a Japanese Dictionary "Nanzando's Medical Dictionary", Mar. 25, 1991, Nanzando Co., Ltd.

Katsuya Fukuyama, at al., "Small angle X-ray Scattering from Glass-like Carbon and its Graphitization Behavior", a Japanese Journal "TANSO" (Carbon), No. 182, pp. 85-90, 1998.

"Colloid Science IV, Experimental Methodology of Colloid. Science", edited by "Nihon-Kagaku-Gakkai" (The Chemical Society of Japan), Apr. 1, 1996, Tokyo Kagaku Dozin Co., Ltd.

M. Shioya, et al., "Characterization of the Structure of Carbon Fibers by Wide-Angle and Small-Angle X-ray Scatterings", a Japanese Journal "TANSO" (Carbon), No. 139, pp. 189-198, 1989.

Keiko Nishikawa, "Study on Pore Structure of Porous Carbons by Small-Angle X-ray Scattering", a Japanese Journal "TANSO" (Carbon), No. 191, pp. 71-76, 2000.

Undated brochure describing the commercial product "Maririn", Gun Ei Chemical Industry Co., Ltd.

No-address Cover letter form for sending a brochure describing the commercial product "Maririn", etc., dated May 8, 2002, Gun Ei Chemical Industry Co., Ltd.

O. Otsubo, et al., "Direct hemoperfusion with non-coated charcoal of high adsorption capacity derived from thermosetting resin", Trans Am Soc Artif Intern Organs, vol. 26, pp. 124-128, 1980.

Hideki Tatsltmoto, et al., "Activated carbon for recovering solvents", a Japanese Text Book "Kassei-Tanso no Oyo-Gijutsu" (Applied Technology of Activated Carbon), pp. 2, 2000.

Hiroshi Kitagawa et al.; Steam Activation of Phenolformaldehyde Resin; Japanese Journal; Kogyo-Kagaju-Zasshi; Journal of Chemistry; vol. 73, No. 10; pp. 2100-2104, 1970.

Shigeaki Kasaoka, et al., "Preparation of Activated Fibrous Carbon from Phenolic Fabric and Its Molecular Sieving Properties", a Japanese Journal "Nihon-KagakuKaishi" (A Chemical Society of Japan), No. 6, pp. 990-1000, 1987.

Hideki Tatsumoto, et al., "Activated carbon for recovering solvents", a Japanese Text Book "Kassei-Tanso no Oyo-Gijutsu" (Applied Technology of Activated Carbon), pp. 2, 2000.

* cited by examiner

ADSORBENT FOR ORAL ADMINISTRATION

CROSS REFERENCE TO RELATED APPLICATION

This application is a Divisional of U.S. application Ser. No. 10/948,314, filed on Sep. 24, 2004, which is a Continuation-In-Part of International Application No. PCT/JP2003/14011 filed on Oct. 31, 2003, which claims benefit of Japanese Application No. 2002-320254, filed on Nov. 1, 2002, the entire disclosures of which are incorporated by reference.

TECHNICAL FIELD

The present invention relates to an adsorbent for oral administration comprising a spherical activated carbon having a specific pore structure, and an adsorbent for oral administration comprising a surface-modified spherical activated carbon prepared by oxidizing and reducing the spherical activated carbon and having a similar specific pore structure.

The adsorbent for oral administration, according to the present invention, exhibits a selective adsorbability, that is, a high adsorbability of harmful toxins, despite a low adsorbability of useful components such as digestive enzymes in a body. Further, the adsorbent has a specific pore structure, and thus, has a greatly improved selective adsorbability in comparison with that of a conventional adsorbent for oral administration. Therefore, the adsorbent for oral administration, according to the present invention, is effective for the treatment of a patient suffering from a liver or renal disease.

BACKGROUND ART

In patients suffering with a lack of a renal function or a liver function, harmful toxic substances are accumulated or formed in bodies, such as blood, with a progress of a disorder of the organ functions, and thus an encephalopathia occurs, such as a disturbance of consciousness or uremia. Yearly, there is a growing number of such patients, and therefore, the development of an organ-substitute apparatus or medicament having a function to remove toxic substances from bodies, in place of such defective organs, has become a serious problem. A method for removing toxic substances by hemodialysis as an artificial kidney is prevalent. Nevertheless, the hemodialysis-based artificial kidney requires a special apparatus, and thus, a skilled specialist is required from a safe operation standpoint. Further, blood must be taken from a patient's body, and thus, there are disadvantages in that patients must bear high physical, mental and economic burdens. Accordingly, hemodialysis is not satisfactory.

Recently, as a means of remedying the above disadvantages, an oral adsorbent which can be orally administered and cure a disorder of renal and liver functions has received considerable attention. Specifically, an adsorbent disclosed in Japanese Examined Patent Publication (Kokoku) No. 62-11611 comprises a porous spherical carbonaceous substance having particular functional groups (hereinafter referred to as a surface-modified spherical activated carbon); having a high safety factor and stable to a body; and having a useful selective adsorbability, that is, an excellent adsorbability of harmful substances in the presence of a bile acid in an intestine, and a low adsorbability of useful substances such as digestive enzymes in the intestine. For these reasons, the oral adsorbent is widely and clinically used for a patient suffering from a disorder of a liver or renal function, as an adsorbent having few side effects such as constipation. The above adsorbent disclosed in Japanese Examined Patent Publication (Kokoku) No. 62-11611 was prepared by forming a spherical activated carbon from a pitch such as a petroleum pitch as a carbon source, and then carrying out an oxidizing treatment and a reducing treatment.

DISCLOSURE OF THE INVENTION

The inventors of the present invention engaged in intensive research to develop an adsorbent for oral administration exhibiting a greater selective adsorbability than that of the above-mentioned oral adsorbent comprising the conventional porous spherical carbonaceous substance prepared by forming a spherical activated carbon from a pitch and oxidizing and reducing the activated carbon, and surprisingly, found that a spherical activated carbon prepared from a thermosetting resin as a carbon source, even without the oxidizing and reducing treatments, exhibits an excellent selective adsorbability; that is, on one hand, an excellent adsorbability of β-aminoisobutyric acid which is one of the uremic substances in a body, and on the other hand, a low adsorbability of useful substances, for example, digestive enzymes, such as α-amylase, and that a level of the selective adsorbability thereof is superior to that of the adsorbent disclosed in Japanese Examined Patent Publication (Kokoku) No. 62-11611. Because the above-mentioned spherical activated carbon prepared from the thermosetting resin as a carbon source exhibits an excellent adsorbability of β-aminoisobutyric acid, it is presumed that the above-mentioned spherical activated carbon has an excellent adsorbability of other toxic substances having a molecular weight similar to that of β-aminoisobutyric acid, for example, octopamine or α-aminobutyric acid, or dimethylamine, aspartic acid, or arginine which is a toxic substance or a precursor thereof in a renal disease, or other water-soluble basic or ampholytic substances.

It was thought that the conventional porous spherical carbonaceous substance, that is, the surface-modified spherical activated carbon used for the adsorbent disclosed in Japanese Examined Patent Publication (Kokoku) No. 62-11611, began to exhibit the selective adsorbability as above, after functional groups were introduced by the oxidizing and reducing treatments of the spherical activated carbon prepared from a pitch. Therefore, it is surprising that the spherical activated carbon prior to the oxidizing and reducing treatments exhibit a selective adsorbability, and the adsorbability per se is superior to that of the conventional adsorbent for oral administration.

Further, the present inventors found that the useful selective adsorbability; that is, on one hand, an excellent adsorbability of β-aminoisobutyric acid which is one of the uremic substances in a body, and on the other hand, a low adsorbability of useful substances, for example, digestive enzymes, such as α-amylase, is improved in a surface-modified spherical activated carbon prepared by oxidizing and reducing the above spherical activated carbon, in comparison with the adsorbent disclosed in Japanese Examined Patent Publication (Kokoku) No. 62-11611. Therefore, it is presumed that the surface-modified spherical activated carbon has a greater adsorbability of other toxic substances having a molecular weight similar to that of β-aminoisobutyric acid, for example, octopamine or α-aminobutyric acid, or dimethylamine, aspartic acid, or arginine which is a toxic substance or a precursor thereof in a renal disease, or other water-soluble basic or ampholytic substances.

The present invention is based on the above findings.

Accordingly, the present invention relates to an adsorbent for oral administration, characterized by comprising a spherical activated carbon, wherein a diameter is 0.01 to 1 mm, a specific surface area determined by Langmuir's adsorption equation is 1000 m²/g or more, and a diffraction intensity ratio, an R value, determined by an equation (1):

$$R=(I_{15}-I_{35})/(I_{24}-I_{35}) \quad (1)$$

wherein $I_{15}$ is a diffraction intensity when a diffraction angle (2θ) of an X-ray diffractometry is 15°, $I_{35}$ is a diffraction intensity when a diffraction angle (2θ) of an X-ray diffractometry is 35°, and $I_{24}$ is a diffraction intensity when a diffraction angle (2θ) of an X-ray diffractometry is 24°, is 1.4 or more.

The present invention also relates to an adsorbent for oral administration, characterized by comprising a surface-modified spherical activated carbon, wherein a diameter is 0.01 to 1 mm, a specific surface area determined by Langmuir's adsorption equation is 1000 m²/g or more, a total amount of acidic groups is 0.40 to 1.00 meq/g, a total amount of basic groups is 0.40 to 1.10 meq/g, and a diffraction intensity ratio, an R value, determined by an equation (1):

$$R=(I_{15}-I_{35})/(I_{24}-I_{35}) \quad (1)$$

wherein $I_{15}$ is a diffraction intensity when a diffraction angle (2θ) of an X-ray diffractometry is 15°, $I_{35}$ is a diffraction intensity when a diffraction angle (2θ) of an X-ray diffractometry is 35°, and $I_{24}$ is a diffraction intensity when a diffraction angle (2θ) of an X-ray diffractometry is 24°, is 1.4 or more.

BEST MODE FOR CARRYING OUT THE INVENTION

The spherical activated carbon or the surface-modified spherical activated carbon used as the adsorbent for oral administration of the present invention has a diffraction intensity ratio (an R value) calculated from an equation (1) of 1.4 or more, as above-mentioned.

First, the diffraction intensity ratio (an R value) will be explained.

Figure 1:
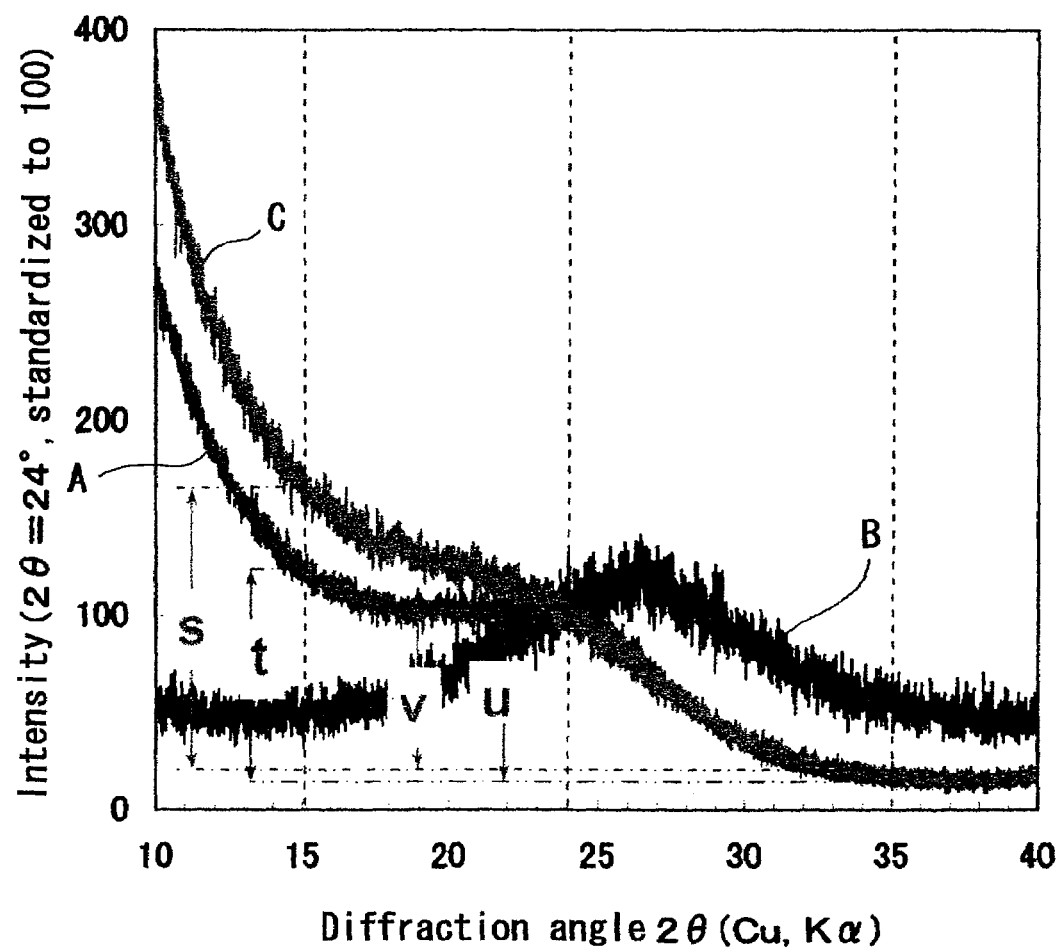
FIG. 1 shows an X-ray diffraction pattern of a surface-modified spherical activated carbon of the prior art (curve A), an X-ray diffraction pattern of a paste product of a surface-modified spherical activated carbon of the prior art (curve B), and an X-ray diffraction pattern of a surface-modified spherical activated carbon used as the adsorbent for oral administration of the present invention (curve C).

When the surface-modified spherical activated carbon prepared by a conventional method disclosed in Examples 1 to 3 in Japanese Examined Patent Publication (Kokoku) No. 62-11611 is investigated by a powder X-ray diffractometry, an X-ray diffraction pattern having the same tendency as that of the curve A shown in FIG. 1 is obtained. The curve A per se is an X-ray diffraction pattern of the surface-modified spherical activated carbon prepared in Comparative Example 1, as mentioned below. As apparent from the curve A, a diffraction peak corresponding to a 002 plane is observed at the diffraction angle (2θ) of around 20° to 30°. The intensity is lowered by a decrease of the diffraction X-ray in the range where the diffraction angle (2θ) is higher than 30°. On the other hand, in the range where the diffraction angle (2θ) is lower than 20°, a strong X-ray is observed even in the range where the diffraction angle (2θ) is lower than 15°, that is, in the range where a diffraction X-ray from 002 plane is rarely observed. Further, when the surface-modified spherical activated carbon prepared by a conventional method disclosed in Examples 1 to 3 in Japanese Examined Patent Publication (Kokoku) No. 62-11611 is investigated by a powder X-ray diffractometry after water is adsorbed, an X-ray diffraction pattern having the same tendency same as that of the curve B shown in FIG. 1 is obtained. The curve B per se is an X-ray diffraction pattern of the surface-modified spherical activated carbon prepared in Comparative Example 1, as mentioned below, after water was adsorbed. As apparent from the curve B, the X-ray intensity of the curve B is considerably lowered in the low angular range in comparison with the curve A. This phenomenon can be interpreted such that the X-ray intensity in the low angular range is influenced by fine pores, and an X-ray scattering intensity is lowered by an adsorption of water into pores.

As shown in Examples, as mentioned below, on the other hand, in the case of the spherical activated carbon or the surface-modified spherical activated carbon prepared by the method found by the present inventors, an X-ray diffraction pattern having the same tendency as that of the curve C shown in FIG. 1 is generally obtained, in the condition that water is not adsorbed. The curve C per se is an X-ray diffraction pattern of the surface-modified spherical activated carbon prepared in Example 1, as mentioned below. That is, a scattering intensity of the curve C in the low angular range where the diffraction angle (2θ) is 15° or less is apparently strong in comparison with that of the curve A. Each of the curves A, B, and C in FIG. 1 is standardized so that the diffraction intensity at the diffraction angle (2θ) of 24° becomes 100.

It is apparent that a porous product with an X-ray diffraction pattern having the same tendency as that of the curve A shown in FIG. 1 has a pore structure different from that of a porous product with an X-ray diffraction pattern having the same tendency as that of the curve C shown in FIG. 1. Further, it is apparent from the comparison of the curve A and the curve B that a scattering intensity observed in a low angular range in the X-ray diffractometry of the surface-modified spherical activated carbon is reflected from the pore structure, and the product having a stronger scattering intensity has more pores. In the relationship between the scattering angle and the pore diameter, it is assumed that the higher the scattering angle, the finer the pore diameter. In order to analyze a pore structure, a method for determining a pore distribution by an adsorption is generally known. In many cases, however, it is difficult to accurately analyze the pore structure in view of differences in a size or shape of the pores, a size of the substances to be adsorbed, adsorbing conditions, and so on. It is an assumption of the present inventors that the scattering intensity around 15° is only slightly influenced by a diffraction X-ray from a 002 plane, influenced by a scattering from the fine pores, and becomes an index indicating the presence of ultra-fine pores which are difficult to find by the adsorption method, and that the presence of such fine pores is advantageous for adsorbing the harmful substance, β-aminoisobutyric acid. That is, the present inventors assume that the higher the scattering intensity at the diffraction angle (2θ) around 15°, the more effective the adsorption of the harmful substance, β-aminoisobutyric acid, for the spherical activated carbon or the surface-modified spherical activated carbon.

Further, as shown in Examples, as mentioned below, the present inventors experimentally confirmed that the spherical activated carbon or the surface-modified spherical activated carbon having an X-ray diffraction pattern with the same tendency as that of the curve C shown in FIG. 1 exhibits a greater selective adsorbability in comparison with the conventional spherical activated carbon or the conventional surface-modified spherical activated carbon having an X-ray diffraction pattern with the same tendency as that of the curve A shown in FIG. 1.

In the present specification, therefore, the spherical activated carbon or the surface-modified spherical activated carbon is defined by the diffraction intensity ratio, the R value, calculated by the equation (1), to clarify the above relationship. In the above equation (1), $I_{15}$ is the diffraction intensity when a diffraction angle (2θ) of an X-ray diffractometry is 15°; that is, in a range where a difference between the diffraction intensity of curve A and that of curve C is increased; $I_{24}$ is a diffraction intensity when a diffraction angle (2θ) of an X-ray diffractometry is 24°, that is, in a range where a difference between the diffraction intensity of curve A and that of curve C is decreased; and $I_{35}$ is a diffraction intensity when a diffraction angle (2θ) of an X-ray diffractometry is 35°, and is used to correct a measurement error between the test samples due to background disturbances.

Therefore, a diffraction intensity ratio, an R value, which is calculated by the equation (1) is $$R=t/u,$$

for the curve A, and $$R=s/v$$

for the curve C.

The present inventors confirmed that a diffraction intensity ratio, an R value, of each of the conventionally known typical surface-modified spherical activated carbons for oral administration is less than 1.4, and did not find any known orally-administrating surface-modified spherical activated carbon having a diffraction intensity ratio, an R value, of 1.4 or more, to the knowledge of the present inventors. Further, as shown in Examples, as mentioned below, the surface-modified spherical activated carbon having a diffraction intensity ratio, an R value, of 1.4 or more, has an improved adsorbability of β-aminoisobutyric acid in comparison with the surface-modified spherical activated carbon having a diffraction intensity ratio, an R value, of less than 1.4, and thus it is apparent that the surface-modified spherical activated carbon having a diffraction intensity ratio, an R value, of 1.4 or more, is useful for the adsorbent for oral administration having an improved selective adsorbability of toxic substances.

The diffraction intensity ratio, the R value, determined by an equation (1) for the spherical activated carbon or the surface-modified spherical activated carbon used for the adsorbent for oral administration according to the present invention is preferably 1.4 or more, more preferably 1.5 or more, most preferably 1.6 or more.

The inventors of the present invention found that the spherical activated carbon or the surface-modified spherical activated carbon having a diffraction intensity ratio, an R value, of 1.4 or more can be prepared, using a thermosetting resin as a carbon source, instead of a pitch used as a carbon source for the conventional adsorbent for oral administration. Alternatively, it can be prepared from a pitch as a carbon source as the conventional adsorbent for oral administration, by developing a cross-linked structure during the treatment imparting infusibility, and disrupting the arrangement of the carbon hexagon network surface.

In the first place, a preparing method using a thermosetting resin as a carbon source will be described.

A spherical material of a thermosetting resin is initially activated at 700 to 1000° C. in reactive gas stream with carbon (for example, steam or carbon dioxide gas) to obtain the spherical activated carbon used as the adsorbent for oral administration of the present invention. The term spherical "activated carbon" as used herein means a porous product prepared by a heat-treatment of a carbon precursor such as a spherical thermosetting resin, and subsequent activation, and having a spherical shape and a specific surface area of 100 m²/g or more, preferably 1000 m²/g or more in the present invention.

If the spherical material of a thermosetting resin is softened by the heat-treatment and changed to an aspheric shape, or fused together by the heat-treatment, the softening can be inhibited by an oxidation at 150° C. to 400° C. in an atmosphere containing oxygen as a treatment imparting infusibility, before the activation as above.

Further, if many pyrolysis gases or the like are generated by the heat-treatment of the spherical thermosetting resin, pyrolysis products may be removed in advance by accordingly carrying out a pre-calcination, prior to the treatment imparting infusibility.

In order to further improve the selective adsorbability of the spherical activated carbon of the present invention, the resulting spherical activated carbon is subsequently oxidized at 300 to 800° C., preferably 320 to 600° C., in an atmosphere containing 0.1 to 50 vol %, preferably 1 to 30 vol %, particularly preferably 3 to 20 vol % of oxygen, and then reduced by a heat-reaction at 800 to 1200° C., preferably 800 to 1000° C., in an atmosphere of non-oxidative gas, to thereby obtain the surface-modified spherical activated carbon used as the adsorbent for oral administration according to the present invention. The term "surface-modified spherical activated carbon" as used herein means a porous product prepared by the oxidizing and reducing treatments of the spherical activated carbon as above, wherein acidic and basic sites are added in a well-balanced manner on the surface of the spherical activated carbon to thereby improve an adsorbability of harmful substances in an intestine.

A particle diameter of the spherical product of a thermosetting resin used as a starting material is preferably about 0.02 to 1.5 mm.

It is important for the thermosetting resin used as the starting material that a spherical product can be formed, and it is not fused or softened, or the shape is not changed, by a heat-treatment at a temperature of 500° C. or less. A thermosetting resin which can avoid a fusion oxidation by the treatment imparting infusibility, such as an oxidation treatment, can be used.

A thermosetting resin which can obtain a high carbonization yield by a heat-treatment is preferable as a starting material. If the carbonization yield is low, a strength of the spherical activated carbon becomes low. Further, undesirable pores are formed and a bulk density of the spherical activated carbon is lowered, and thus, a specific surface area per volume is lowered. Therefore, a volume to be orally administered is increased, and thus, a problem arises in that an oral administration becomes difficult. Accordingly, a thermosetting resin having a higher carbonization yield is preferable. A yield by a heat-treatment at 800° C. in an atmosphere of non-oxidative gas is preferably 40% by weight or more, more preferably 45% by weight or more.

The thermosetting resin used as a starting material may be, for example, a phenolic resin, such as a novolak phenolic resin, a resol phenolic resin, a novolak alkylphenolic resin, or a resol alkylphenolic resin, or a furan resin, a urea resin, a melamine resin, or an epoxy resin. A copolymer of divinylbenzene and styrene, acrylonitrile, acrylic acid, or methacrylic acid may be used as the thermosetting rein.

Further, an ion-exchange resin may be used as the thermosetting resin. Generally, an ion-exchange resin comprises a copolymer of divinylbenzene and styrene, acrylonitrile, acrylic acid, or methacrylic acid, that is, a thermosetting resin, and essentially has a structure wherein ion-exchange groups are bonded to a copolymer matrix having a three-dimensional network skeleton. The ion-exchange resin is generally classified, with respect to the kinds of ion-exchange groups, into a strongly acidic ion-exchange resin having sulfonic acid groups, a weakly acidic ion-exchange resin having carboxylic or sulfonic acid groups, a strongly basic ion-exchange resin having quaternary ammonium salts, and a weakly basic ion-exchange resin having primary or tertiary amines. In addition, so-called hybrid ion-exchange resin having both acidic and basic ion-exchange groups is included as a special ion-exchange resin. In the present invention, all of the above ion-exchange resins may be used as a starting material, but a phenolic resin is preferably used.

Then, a method for preparing the spherical activated carbon or the surface-modified spherical activated carbon used as the adsorbent for oral administration from a pitch as a carbon source, by developing a cross-linked structure during the treatment imparting infusibility, and disrupting the arrangement of the carbon hexagon network plane will be described.

First, a dicyclic or tricyclic aromatic compound or a mixture thereof having a boiling point of 200° C. or more is added as an additive to a pitch such as a petroleum pitch or a coal pitch. The whole is heated and mixed, and then shaped to obtain a shaped pitch. The spherical activated carbon or the surface-modified spherical activated carbon is for oral administration, and the raw material must have a sufficient purity from a safety standpoint, and have stable properties.

Thereafter, the shaped pitch is dispersed and granulated in hot water, with stirring, to obtain a microspherical shaped pitch. Further, the additive is extracted and removed from the shaped pitch by a solvent having a low solubility to the pitch but a high solubility to the additive. The resulting porous pitch is oxidized by an oxidizing agent to obtain a porous pitch having an infusibility to a heat. The resulting infusible porous pitch is treated in a gas flow such as steam or carbon dioxide gas reactive with carbon to obtain the spherical activated carbon.

Then, the resulting spherical activated carbon is oxidized by heating in an atmosphere containing oxygen, and thereafter, reduced in an atmosphere of a non-oxidizable gas to obtain the surface-modified spherical activated carbon used as the adsorbent for oral administration according to the present invention.

In the above method for the preparation, the atmosphere containing oxygen in the particular amount may be pure oxygen, or nitrogen oxides or air as the oxygen source. As the atmosphere inert against carbon, for example, nitrogen, argon or helium may be used alone or in the form of a mixture thereof.

The purposes of the addition of the aromatic compound to the raw pitch are that a flowability of the raw pitch is enhanced, whereby the granulation thereof is made easier, and the porous pitch is produced by extracting and removing the additive from the shaped pitch, whereby a structure control and a calcination of the carbonaceous material by oxidization in the subsequent steps is made easier. As the additive, for example, naphthalene, methylnaphthalene, phenylnaphthalene, benzyl-naphthalene, methylanthracene, phenanthrene, or biphenyl may be used alone or in a mixture thereof. An amount of the additive added to the pitch is preferably 10 to 50 parts by weight of the aromatic compound with respect to 100 parts by weight of the pitch.

It is preferable that the pitch and the additive are mixed under a melted condition with heating, to achieve a homogeneous mixing. Further, it is preferable that the mixture of the pitch and the additive is shaped to form particles having a particle size of about 0.01 to 1 mm, to control the particle size (diameter) of the resulting spherical activated carbon or the surface-modified spherical activated carbon. The shaping may be conducted during the melted condition, or by grinding the mixture after it has cooled.

A preferable solvent used to extract and remove the additive from the mixture of the pitch and the additive may be, for example, an aliphatic hydrocarbon, such as butane, pentane, hexane, or heptane, a mixture comprising an aliphatic hydrocarbon as a main component, such as naphtha or kerosene, or an aliphatic alcohol, such as methanol, ethanol, propanol, or butanol.

The additive may be removed from the shaped mixture by extracting the additive with the solvent from the shaped mixture of the pitch and the additive, while maintaining the shape. It is assumed that, upon the extraction, through-holes of the additive are formed in the shaped product, and a shaped pitch having a uniform porosity can be obtained.

Then, the resulting porous shaped pitch is subjected to a treatment imparting non-fusibility, that is, the resulting porous shaped pitch is oxidized by an oxidizing agent, preferably at room temperature to 300° C. to obtain the porous infusible shaped pitch having a non-fusibility to heat. As the oxidizing agent, for example, oxygen gas ($O_2$), or a gas mixture prepared by diluting oxygen gas ($O_2$) with air or nitrogen may be used.

The spherical activated carbon or the surface-modified spherical activated carbon used as the adsorbent for oral administration of the present invention is produced by, for example, the above methods using the thermosetting resin or a pitch as a starting material, and has a diameter of 0.01 to 1 mm. If the diameter of the spherical activated carbon or the surface-modified spherical activated carbon is less than 0.01 mm, an exterior surface area of the spherical activated carbon or the surface-modified spherical activated carbon is increased, and useful substances such as digestive enzymes are easily adsorbed. That is unfavorable. When the diameter is more than 1 mm, a diffusion distance of toxic substances into the inside of the spherical activated carbon or the surface-modified spherical activated carbon is increased, and an adsorption rate is lowered. That, too, is unfavorable. The diameter is preferably 0.02 to 0.8 mm. The expression that "a diameter is Dl to Du" as used herein means that a screen passing percentage (%) in a range of a screen opening Dl to Du is 90% or more in a particle-sizes accumulating standard curve prepared in accordance with JIS K 1474, as mentioned below in relation with a method for determining an average particle diameter.

In the spherical activated carbon or the surface-modified spherical activated carbon used as the adsorbent for oral administration of the present invention, a specific surface area (referred to as "SSA" hereinafter) determined by Langmuir's adsorption equation is 1000 m$^2$/g or more. When the spherical activated carbon or the surface-modified spherical activated carbon has an SSA of less than 1000 m$^2$/g, an adsorbability of toxic substances is unfavorably lowered. The SSA is preferably 1000 m$^2$/g or more. The upper limit of the SSA is not particularly limited, but the SSA is preferably 3000 m$^2$/g or less in view of a bulk density and strength.

In the spherical activated carbon or the surface-modified spherical activated carbon used as the adsorbent for oral administration of the present invention, a pore volume within a scope of specific pore diameters is not particularly limited. For example, the above-mentioned Japanese Examined Patent Publication (Kokoku) No. 62-11611 discloses an adsorbent comprising a surface-modified spherical activated carbon wherein a volume of voids having a pore radius of 100 to 75000 angstrom, that is, a volume of pores having a diameter of 20 to 15000 nm, is 0.1 to 1 mL/g. However, in the spherical activated carbon or the surface-modified spherical activated carbon used as the adsorbent for oral administration of the present invention, a volume of pores having a diameter of 20 to 15000 nm may be 0.1 to 1 mL/g, or 0.1 mL/g or less. When a volume of pores having a diameter of 20 to 1000 nm is more than 1 mL/g, an adsorbed amount of useful substances, such as digestive enzymes, may be increased. Therefore, a volume of pores having a diameter of 20 to 1000 nm is preferably 1 mL/g or less.

In the spherical activated carbon or the surface-modified spherical activated carbon used as the adsorbent for oral administration of the present invention, a volume of pores having a diameter of 7.5 to 15000 nm is preferably less than 0.25 mL/g, more preferably 0.2 mL/g or less, as a more excellent selective adsorbability is thus obtained.

In a constitution of functional groups of the surface-modified spherical activated carbon, that is, the product prepared by oxidizing and reducing the spherical activated carbon, which is used as the adsorbent for oral administration of the present invention, a total amount of acidic groups is 0.40 to 1.00 meq/g, and a total amount of basic groups is 0.40 to 1.10 meq/g. When the constitution of functional groups satisfies the condition that a total amount of acidic groups is 0.40 to 1.00 meq/g, and a total amount of basic groups is 0.40 to 1.00 meq/g, the selective adsorbability is improved, and particularly, the adsorbability of harmful substances is favorably enhanced. In the constitution of functional groups, a total amount of acidic groups is preferably 0.40 to 0.90 meq/g, and a total amount of basic groups is preferably 0.40 to 1.00 meq/g.

When the adsorbent of the present invention is used as an agent for treating or preventing a liver or renal disease, a preferable functional-groups constitution is that the total amount of acidic groups is 0.40 to 1.00 meq/g, the total amount of basic groups is 0.40 to 1.10 meq/g, a phenolic hydroxyl group is 0.20 to 0.70 meq/g, and a carboxyl group is 0.15 meq/g or less, and a ratio (a/b) of the total amount of acidic groups (a) to the total amount of basic groups (b) is 0.40 to 2.5, and a relation [(b+c)−d] between the total amount of basic groups (b), the phenolic hydroxyl group (c), and the carboxyl group (d) is 0.60 or more.

Properties of the spherical activated carbon or the surface-modified spherical activated carbon used as the adsorbent for oral administration of the present invention, namely, the average particle diameter, the specific surface area, the pore volume, the total amount of acidic groups, and the total amount of basic groups are measured by the following methods.

(1) An Average Particle Diameter

A particle-sizes accumulating standard curve is prepared in accordance with JIS K 1474 for the spherical activated carbon or the surface-modified spherical activated carbon. The average particle diameter is determined from a screen opening (mm) at an intersection point with a line that is horizontal to an abscissa axis and starts from an intersection point in the particle-sizes accumulating standard curve with a perpendicular line from a 50% point of the abscissa axis.

(2) A Specific Surface Area

An amount of gas adsorbed is measured by a specific surface area measuring apparatus (for example, ASAP2010 manufactured by MICROMERITICS) in accordance with a gas adsorbing method for the spherical activated carbon sample or the surface-modified spherical activated carbon sample, and a specific surface area can be calculated by Langmuir's adsorption equation. More particularly, the spherical activated carbon or the surface-modified spherical activated carbon is charged as a sample in a sample tube, and dried under reduced pressure at 300° C. Thereafter, a weight of dried sample is measured. Then, the test tube is cooled to −196° C., and nitrogen is introduced into the test tube, whereby nitrogen is adsorbed to the spherical activated carbon sample or the surface-modified spherical activated carbon sample. A relation of a nitrogen partial pressure and an adsorbed amount (absorption-isotherm line) is measured.

Langmuir's plotting is carried out, given that a relative pressure of nitrogen is p, and an adsorbed amount at that time is v (cm$^3$/g STP). That is, the plotting in a range wherein p is 0.05 to 0.3 is carried out, in the field wherein a longitudinal axis is p/v, and an abscissa axis is p. Given that the gradient at that time is b (g/cm$^3$), a specific surface area S (unit=m$^2$/g) can be calculated from the equation:

$$S = \frac{MA \times (6.02 \times 10^{23})}{22414 \times 10^{18} \times b}$$

wherein MA denotes a cross-sectional area of a nitrogen molecule, and is 0.162 nm$^2$.

(3) A Pore Volume by a Mercury Press-Injection Method

The pore volume can be measured by a mercury porosimeter (for example, AUTOPORE 9200 manufactured by MICROMERITICS). The spherical activated carbon or the surface-modified spherical activated carbon is charged as a sample in a sample vessel, and degassed under a pressure of 2.67 Pa or less for 30 minutes. Then, mercury is introduced into the sample vessel, a pressure applied is gradually increased (maximum pressure=414 MPa) to force the mercury into the micropores in the spherical activated carbon sample or the surface-modified spherical activated carbon sample. A pore volume distribution of the spherical activated carbon sample or the surface-modified spherical activated carbon sample is measured from a relationship between the pressure and an amount of forced mercury, by equations as mentioned below.

Specifically, a volume of mercury inserted into the spherical activated carbon sample or the surface-modified spherical activated carbon sample while a pressure applied is increased from a pressure (0.06 MPa) corresponding to a pore diameter of 22 μm to the maximum pressure (414 MPa) corresponding to a pore diameter of 3 nm is measured. A pore diameter can be calculated as follows. When mercury is forced into a cylindrical micropore having a diameter (D) by applying a pressure (P), a surface tension (γ) of mercury is balanced with a pressure acting on a section of the micropore, and thus, the following equation is held:

$$-\pi D \gamma \cos \theta = \pi (D/2)^2 \cdot P$$

wherein θ is a contact angle of mercury and a wall of the micropore. Therefore, the following equation:

$$D = (-4\gamma \cos \theta)/P$$

is held.

In the present specification, the relationship between the pressure (P) and the pore diameter (D) is calculated by the equation:

$$D = 1.27/P$$

given that a surface tension of mercury is 484 dyne/cm, a contact angle of mercury and carbon is 130°, a unit of the pressure P is MPa, and a unit of the pore diameter D is μm. The volume of pores having a pore diameter of 20 to 1000 nm in the present invention corresponds to a volume of mercury inserted by applying a pressure increasing from 1.27 MPa to 63.5 MPa.

(4) Diffraction Intensity Ratio, R Value

A spherical activated carbon sample or a surface-modified spherical activated carbon sample is dried at 120° C. for 3 hours under reduced pressure, and charged in an aluminum sample plate, that is, a plate (35×50 mm$^2$; t=1.5 mm) having an opening of 20×18 mm$^2$. Then, diffraction intensities $I_{15}$, $I_{24}$, and $I_{35}$ at diffraction angles (2θ) of 15°, 24°, and 35° are measured by a reflection type x-ray diffractometer method, using a CuKα ray (wave length, λ=0.15418) monochromatized by a graphite monochrometor, as a radiation source. The conditions of an X-ray generating device and a slit are as follows: voltage applied=40 kV, current=100 mA, divergent slit=½°, photo-receiver slit=0.15 mm, and scattering slit=½°. The diffraction pattern was not corrected with respect to a Lorentz polarization factor, absorption factor, atomic scattering factor or the like, but the diffraction angle was corrected, using (111) diffraction line of high-purity silicon powder for a standard substance.

(5) Total Amount of Acidic Groups

The total amount of acidic groups is an amount of NaOH consumed, which may be determined by adding 1 g of the spherical activated carbon sample or the surface-modified spherical activated carbon sample, after being crushed to form particles having a size of 200 mesh or less, to 50 mL of a 0.05N NaOH solution; shaking the mixture for 48 hours; then filtering out the spherical activated carbon sample or the surface-modified spherical activated carbon sample; and titrating until neutralization.

(6) Total Amount of Basic Groups

The total amount of basic groups is an amount of HCl consumed, which may be determined by adding 1 g of the spherical activated carbon sample or the surface-modified spherical activated carbon sample after being crushed to form particles having a size 200 mesh or less, to 50 mL of a 0.05N HCl solution; shaking the mixture for 24 hours; then filtering out the spherical activated carbon sample or the surface-modified spherical activated carbon sample; and titrating until neutralization.

As shown in Examples mentioned as below, the spherical activated carbon or the surface-modified spherical activated carbon used as the adsorbent for oral administration of the present invention exhibits an excellent selective adsorbability, that is, an excellent adsorbability of exacerbation factors of liver diseases or harmful substances of renal diseases, but a lower adsorbability of useful substances such as digestive enzymes, and therefore, may be used as an adsorbent for oral administration for treating or preventing a renal disease or a liver disease.

As the renal disease, there may be mentioned, for example, chronic renal failure, acute renal failure, chronic pyelonephritis, acute pyelonephritis, chronic nephritis, acute nephritic syndrome, acute progressive nephritic syndrome, chronic nephritic syndrome, nephrotic syndrome, nephrosclerosis, interstitial nephritis, tubulopathy, lipoid nephrosis, diabetic nephropathy, renovascular hypertension, or hypertension syndrome, or secondary renal diseases caused by these primary diseases, or a light renal failure before a dialysis therapy, and may be used in an improvement of a light renal failure before a dialysis therapy or a disease condition for a patient during a dialysis therapy (see "Clinical Nephrology", Asakura-shoten, Nishio Honda, Kenkichi Koiso, and Kiyoshi Kurokawa, 1990; and "Nephrology" Igaku-shoin, Teruo Omae and Sei Fujimi, ed., 1981).

As the liver disease, there may be mentioned, for example, fulminant hepatitis, chronic hepatitis, viral hepatitis, alcoholic hepatitis, hepatic fibrosis, liver cirrhosis, hepatic cancer, autoimmune hepatitis, drug allergic hepatopathy, primary biliary cirrhosis, tremor, encephalopathia, dysbolism, or dysfunction. Further, the porous spherical carbonaceous substance can be used in a treatment of a disease caused by toxic substances in a body, such as psychosis.

Further, as shown in Examples, the spherical activated carbon or the surface-modified spherical activated carbon used as the adsorbent for oral administration of the present invention has an excellent adsorbability of β-aminoisobutyric acid which is one of the uremic substances in a body, and therefore, may be preferably used as an adsorbent for oral administration for treating or preventing a disease bearing a relationship to or deteriorated by uremic substances, such as a chronic renal failure or a complicated disease thereof. As the complications of the chronic renal failure, there may be mentioned, for example, a disease of a circulatory system, such as cardiac insufficiency, arrhythmia, hypertension, or ischemic heart disease; a vascular lesion, such as arterial sclerosis including vascular calcification, or arteriosclerosis obliterans; a cerebrovascular accident; an anemia, such as renal anemia, or erythropoietin-resistant anemia; bone- or calcium-dysbolism or dialysis osteopathy, such as secondary hyperparathyroidism, aplastic bone, anomalous calcification; a dialysis amyloidosis including amyloid spondylosis; a trophic syndrome; a lipid-dysbolism; or an itch.

Therefore, when the adsorbent for oral administration is used as an agent for treating or preventing a renal disease, it contains the spherical activated carbon or the surface-modified spherical activated carbon as an effective component. When the adsorbent for oral administration according to the present invention is used as an agent for a treatment of a liver or renal disease, a dosage thereof depends on the subject (human or other animal), age, individual differences, disease conditions, and so on. Therefore, in some cases, a dosage outside of the following dosage may be appropriate, but in general, the oral dosage in the case of a human is usually 1 to 20 g of the adsorbent per day, wherein the daily dosage may be divided into three to four portions. The dosage may appropriately vary with the disease conditions. The formulation may be administered in any form, such as powders, granules, tablets, sugar-coated tablets, capsules, suspensions, sticks, divided packages, or emulsions. In the case of capsules, the usual gelatin capsules, or if necessary, enteric capsules may be used. In the case of tablets, the formulations must be broken into the original fine particles inside the body. The adsorbent may be used as a mixture with an electrolyte-controlling agent, such as an aluminum gel or Kayexalate.

EXAMPLES

The present invention now will be further illustrated by, but is by no means limited to, the following Examples.

In the following Examples, an adsorption test of α-amylase and an adsorption test of DL-β-aminoisobutyric acid were carried out in accordance with the following methods, and the selective adsorption rate was calculated by the following method.

(1) Adsorption Test of α-Amylase

The spherical activated carbon sample or the surface-modified spherical activated carbon sample was dried, and 0.125 g of the dried sample was accurately weighed and charged into a conical flask equipped with a ground-in stopper. On the other hand, 0.100 g of α-amylase (liquefied type) was accurately weighed and dissolved by adding a phosphate buffer (pH 7.4) to prepare a stock solution having an accurate volume of 1000 mL. The stock solution in an accurate amount of 50 mL was charged to the conical flask equipped with a ground-in stopper. The flask was shaken at 37±1° C. for 3 hours. The product in the flask was filtered with suction through a 0.65 μm membrane filter. A first filtrate (about 20 mL) was discarded, and a subsequent filtrate (about 10 mL) was taken as a sample solution.

Further, the same procedures were repeated except that only a phosphate buffer (pH 7.4) was used, to obtain a filtrate as a correction solution. The sample solution and the correction solution were analyzed by an absorptiometeric analysis, using a phosphate buffer (pH 7.4) as a control. The absorbance at a wavelength of 282 nm was measured. A difference between the absorbance of the sample solution and the absorbance of the correction solution was taken as a test absorbance.

A standard curve was prepared by adding the α-amylase stock solution in an accurate amount of 0 mL, 25 mL, 50 mL, 75 mL, or 100 mL to a measuring flask, adding a phosphate buffer (pH 7.4) to 100 mL, and measuring an absorbance at a wave length of 282 nm. From the test absorbance and the standard curve, an amount (mg/dL) of α-amylase remaining in the solution was calculated.

To measure a dependence on an amount of the spherical activated carbon sample or the surface-modified spherical activated carbon sample, the same procedures were repeated except that an amount of the spherical activated carbon sample or the surface-modified spherical activated carbon sample used was 0.500 g, and the test absorbance was measured and the amount of α-amylase remaining in the solution was calculated as above.

(2) Adsorption Test of DL-β-Aminoisobutyric Acid

The spherical activated carbon sample or the surface-modified spherical activated carbon sample was dried, and 2.500 g of the dried sample was accurately weighed and charged into a conical flask equipped with a ground-in stopper. On the other hand, 0.100 g of DL-β-aminoisobutyric acid was accurately weighed and dissolved by adding a phosphate buffer (pH 7.4) to prepare a stock solution having an accurate volume of 1000 mL. The stock solution in an accurate amount of 50 mL was charged to the conical flask equipped with a ground-in stopper. The flask was shaken at 37±1° C. for 3 hours. The product in the flask was filtered with suction through a 0.65 μm membrane filter. A first filtrate (about 20 mL) was discarded, and a subsequent filtrate (about 10 mL) was taken as a sample solution.

Then, 0.1 mL of the sample solution was accurately weighed and charged in a test tube. A phosphate buffer (pH 8.0) was added in an accurate amount of 5 mL thereto, and the whole was mixed. Thereafter, a solution prepared by dissolving 0.100 g of fluorescamine in 100 mL of acetone (for a non-aqueous titration) was added in an accurate amount of 1 mL, and the whole was mixed and allowed to stand for 15 minutes. The resulting solution was analyzed by fluorometry, and the fluorescence was measured at an exciting wavelength of 390 nm and a fluorescent wavelength of 475 nm.

A standard curve was prepared by producing 100 mL of a mixture of 0 mL, 15 mL, 50 mL, 75 mL, and 100 mL of the DL-β-aminoisobutyric acid stock solution and the balance of a phosphate buffer (pH 7.4), stirring and filtering the mixture, charging the resulting filtrate in an accurate amount of 0.1 mL to a test tube, adding a phosphate buffer (pH 8.0) in an accurate amount of 5 mL, mixing the whole, adding a solution (an accurate amount: 1 mL) prepared by dissolving 0.100 g of fluorescamine in 100 mL of acetone (for a non-aqueous titration), mixing the whole, allowing to stand for 15 minutes, analyzing the resulting solution by fluorometry, and measuring the fluorescence at an exciting wavelength of 390 nm and a fluorescent wavelength of 475 nm. Finally, an amount (mg/dL) of DL-β-aminoisobutyric acid remaining in the solution was calculated, using the standard curve.

To measure a dependence on an amount of the spherical activated carbon sample or the surface-modified spherical activated carbon sample, the same procedures were repeated except that an amount of the spherical activated carbon sample or the surface-modified spherical activated carbon sample used was 0.500 g, and the test fluorescence was measured and the amount of DL-β-aminoisobutyric acid remaining in the solution was calculated as above.

(3) The Selective Adsorption Rate

The selective adsorption rate was calculated from an amount of α-amylase remaining in the solution in the adsorption test of α-amylase wherein an amount of the spherical activated carbon sample used or the surface-modified spherical activated carbon sample used was 0.500 g, and an amount of DL-β-aminoisobutyric acid remaining in the solution in the adsorption test of DL-β-aminoisobutyric acid, wherein an amount of the spherical activated carbon sample used or the surface-modified spherical activated carbon sample used was 0.500 g, using the equation:

$$A = (10 - Tr)/(10 - Ur)$$

wherein A denotes the selective adsorption rate, and Tr denotes an amount of DL-β-aminoisobutyric acid remaining in the solution, and Ur denotes an amount of α-amylase remaining in the solution.

Example 1

Spherical phenolic resin (particle diameter=10 to 700 μm: trade name=High functional true spherical resin "Markin" HF500 type; Gun Ei Chemical Industry Co., Ltd.) was sieved through a screen having an opening size of 250 μm, to remove fine powders. Then, 150 g of the resulting spherical phenolic resin was charged into a vertical reaction quartz tube having a grating, heated to 350° C. over 1.5 hours under a nitrogen gas stream, and further heated to 900° C. over 6 hours, and maintained at 900° C. for 1 hour to obtain 68.1 g of a spherical carbonaceous material. Thereafter, the product was activated at 900° C. at an atmosphere of a gas mixture of nitrogen gas (3 NL/min) and steam (2.5 NL/min). When a packing density of the spherical activated carbon was lowered to 0.5 mL/g, the activation was ceased to obtain 29.9 g of the spherical activated carbon (yield=19.9% by weight).

Diffraction intensities of the resulting spherical activated carbon were 743 cps at a diffraction angle (2θ) of 15°, 90 cps at a diffraction angle (2θ) of 35°, and 473 cps at a diffraction angle (2θ) of 24°. Therefore, a diffraction intensity ratio, an R value, was 1.71.

The properties of the resulting spherical activated carbon are listed in Tables 1 and 2.

The curve C in FIG. 1 is a diffraction curve obtained by measuring an intensity of the product prepared by vacuum drying the spherical activated carbon obtained in Example 1 at 120° C. for 2 hours, by the same procedures as those mentioned in the method for measuring a diffraction intensity ratio, an R value.

Example 2

The procedure described in Example 1 was repeated, except that a spherical phenolic resin (particle diameter=700

µm: trade name=Spherical cured phenolic resin ACS series PR-ACS-2-50C; Sumitomo Bakelite Co., Ltd.) was used instead of the spherical phenolic resin used in Example 1, i.e., the spherical phenolic resin manufactured by Gunei Kagaku K.K., to obtain the spherical activated carbon (yield=26.5%).

Diffraction intensities of the resulting spherical activated carbon were 788 cps at a diffraction angle ($2\theta$) of 15°, 72 cps at a diffraction angle ($2\theta$) of 35°, and 492 cps at a diffraction angle ($2\theta$) of 24°. Therefore, a diffraction intensity ratio, an R value, was 1.71.

The properties of the resulting spherical activated carbon are listed in Tables 1 and 2.

Example 3

The spherical activated carbon obtained in Example 1 was oxidized at 470° C. for 3 hours and 15 minutes on a fluidized bed at an atmosphere of a gas mixture of nitrogen gas and oxygen gas (oxygen concentration=18.5 vol %), and then, reduced at 900° C. for 17 minutes on the fluidized bed at an atmosphere of nitrogen gas to obtain the surface-modified spherical activated carbon.

Diffraction intensities of the resulting surface-modified spherical activated carbon were 627 cps at a diffraction angle ($2\theta$) of 15°, 66 cps at a diffraction angle ($2\theta$) of 35°, and 400 cps at a diffraction angle ($2\theta$) of 24°. Therefore, a diffraction intensity ratio, an R value, was 1.68.

The properties of the resulting surface-modified spherical activated carbon are listed in Tables 1 and 2.

Example 4

The procedure described in Example 3 was repeated, except that the spherical activated carbon used in Example 2 was used as the starting material, to obtain the surface-modified spherical activated carbon.

Diffraction intensities of the resulting surface-modified spherical activated carbon were 702 cps at a diffraction angle ($2\theta$) of 15°, 74 cps at a diffraction angle ($2\theta$) of 35°, and 428 cps at a diffraction angle ($2\theta$) of 24°. Therefore, a diffraction intensity ratio, an R value, was 1.77.

The properties of the resulting surface-modified spherical activated carbon are listed in Tables 1 and 2.

Example 5

The procedure described in Example 3 was repeated, except that an ion-exchange resin (styrene based; effective diameter=0.50 to 0.65 mm; trade name=Amberlite 15WET; Organo Corporation) was used instead of the phenolic resin, to obtain the surface-modified spherical activated carbon.

Diffraction intensities of the resulting surface-modified spherical activated carbon were 765 cps at a diffraction angle ($2\theta$) of 15°, 82 cps at a diffraction angle ($2\theta$) of 35°, and 485 cps at a diffraction angle ($2\theta$) of 24°. Therefore, a diffraction intensity ratio, an R value, was 1.69.

The properties of the resulting surface-modified spherical activated carbon are listed in Tables 1 and 2.

Figure 2:
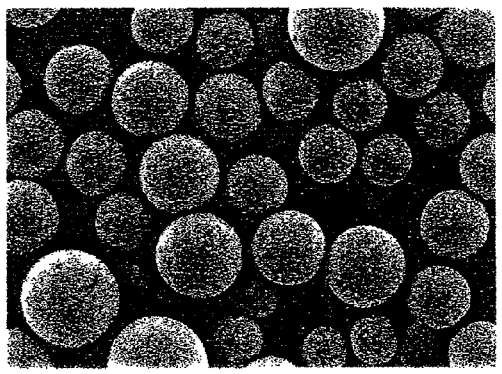
FIG. 2 is a micrograph (magnification: ×50) illustrating a surface structure of a surface-modified spherical activated carbon of the present invention obtained by a scanning electron microscope.
Figure 3:
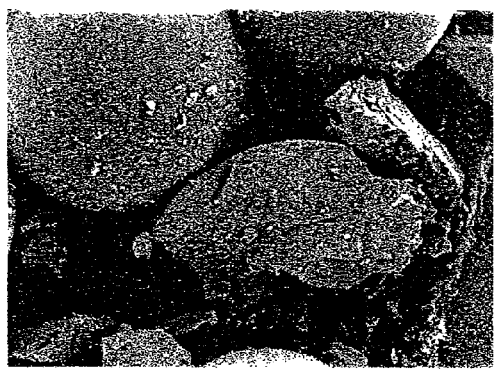
FIG. 3 is a micrograph (magnification: ×200) illustrating a cross sectional structure of sectional structure of a surface-modified spherical activated carbon of the present invention obtained by a scanning electron microscope.

Further, a micrograph (magnification=×50) illustrating a surface structure of the resulting surface-modified spherical activated carbon obtained by a scanning electron microscope is shown in FIG. 2, and a micrograph (magnification=×200) illustrating a cross sectional structure of the resulting surface-modified spherical activated carbon obtained by a scanning electron microscope is shown in FIG. 3.

Comparative Example 1

Petroleum pitch (68 kg) (softening point=210° C.; quinoline insoluble contents=not more than 1% by weight; ratio of hydrogen atoms/carbon atoms=0.63) and naphthalene (32 kg) were charged into an autoclave (internal volume=300 L) equipped with stirring fans, melted at 180° C., and mixed. The mixture was extruded at 80 to 90° C. to form string-like shaped products. Then, the string-like shaped products were broken so that a ratio of a diameter to a length became about 1 to 2.

The resulting broken products were added to an aqueous solution prepared by dissolving 0.23% by weight of polyvinyl alcohol (saponification value=88%) and heating to 93° C., and dispersed with stirring to be spheroidized. Then, the whole was cooled by replacing the polyvinyl alcohol aqueous solution with water, at 20° C. for 3 hours, whereby the pitch was solidified and naphthalene crystals were precipitated, and a slurry of spherical shaped products of pitch was obtained.

After most of the water was removed by filtration, the naphthalene in the pitch was extracted and removed with n-hexane at an amount of about 6 times that of the spherical shaped products of pitch. The resulting porous spherical pitch was heated to 235° C. by passing a heated air in a fluidized bed, and allowed to stand at 235° C. for 1 hour, to thereby be oxidized, and a porous spherical oxidized pitch was obtained, which is non-fusible to heat. The resulting porous spherical oxidized pitch had an oxygen content of 14% by weight.

Thereafter, the resulting porous spherical oxidized pitch was activated in a fluidized bed at 900° C. for 170 minutes by a nitrogen gas atmosphere containing 50% by volume of steam to obtain a spherical activated carbon. Further, the resulting spherical activated carbon was oxidized in the fluidized bed at 470° C. for 195 minutes by a nitrogen-oxygen atmosphere containing 18.5% by volume of oxygen, and reduced in the fluidized bed at 900° C. for 17 minutes by a nitrogen gas atmosphere, to obtain a surface-modified spherical activated carbon.

Diffraction intensities of the resulting surface-modified spherical activated carbon were 647 cps at a diffraction angle ($2\theta$) of 15°, 84 cps at a diffraction angle ($2\theta$) of 35°, and 546 cps at a diffraction angle ($2\theta$) of 24°. Therefore, a diffraction intensity ratio, an R value, was 1.22.

The properties of the resulting surface-modified spherical activated carbon are listed in Tables 1 and 2.

The curve A in FIG. 1 is a diffraction curve obtained by measuring an intensity of the product prepared by vacuum drying the surface-modified spherical activated carbon obtained in Comparative Example 1 at 120° C. for 2 hours, by the same procedures as those mentioned in the method for measuring a diffraction intensity ratio, an R value; and the curve B in FIG. 1 is a diffraction curve obtained by measuring an intensity of the paste product prepared by adding 2 or 3 drops of ion-exchange water dropwise to 200 mg of the surface-modified spherical activated carbon obtained in Comparative Example 1, by the procedures mentioned as above.

Figure 4:
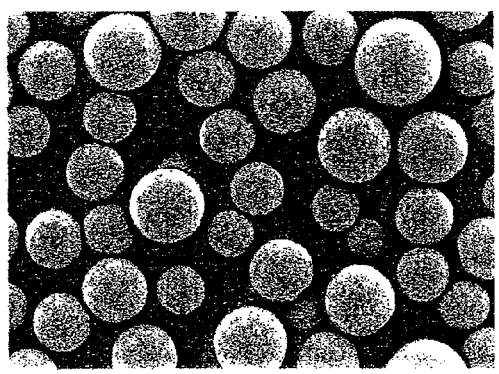
FIG. 4 is a micrograph (magnification: ×50) illustrating a surface structure of a surface-modified spherical activated carbon of the prior art obtained by a scanning electron microscope.
Figure 5:
FIG. 5 is a micrograph (magnification: ×200) illustrating a cross sectional structure of sectional structure of a surface-modified spherical activated carbon of the prior art obtained by a scanning electron microscope.
Figure 6:
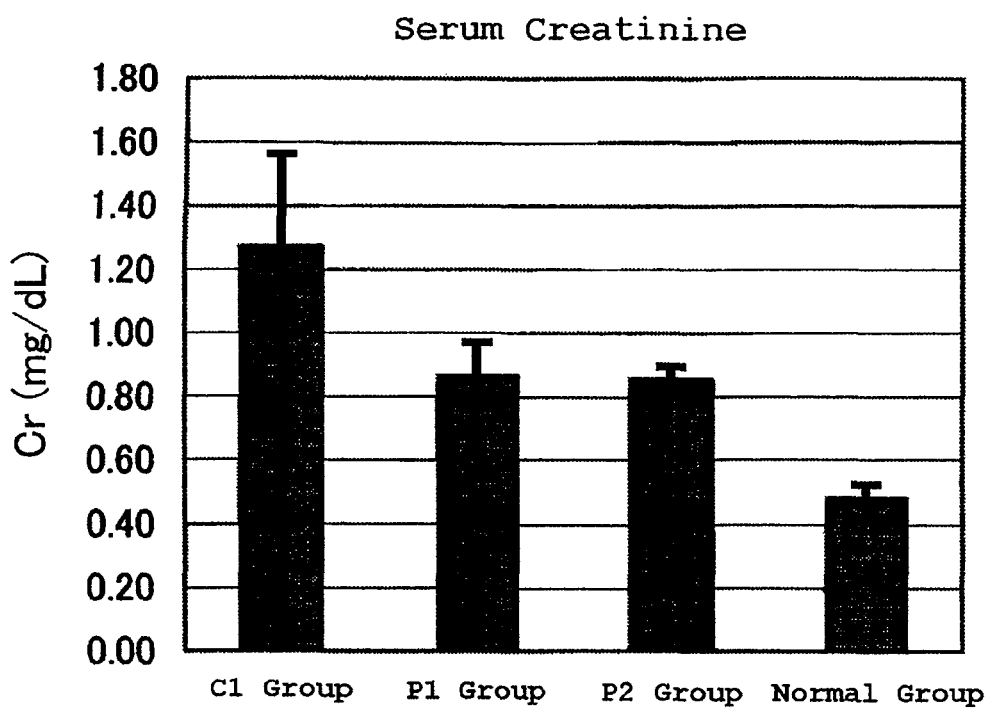
FIG. 6 is a graph showing the results of the investigation of the effect of the adsorbent for oral administration of the present invention on serum creatinine.

Further, a micrograph (magnification: ×50) illustrating a surface structure of the resulting surface-modified spherical activated carbon obtained by a scanning electron microscope is shown in FIG. 4, and a micrograph (magnification: ×200) illustrating a cross sectional structure of the resulting surface-modified spherical activated carbon obtained by a scanning electron microscope is shown in FIG. 5.

Comparative Example 2

The procedure described in Comparative Example 1 was repeated, except that the oxidizing and reducing treatment of the spherical activated carbon were not carried out, to obtain the spherical activated carbon.

Diffraction intensities of the resulting surface-modified spherical activated carbon were 651 cps at a diffraction angle ($2\theta$) of 15°, 81 cps at a diffraction angle ($2\theta$) of 35°, and 548 cps at a diffraction angle (2θ) of 24°. Therefore, a diffraction intensity ratio, an R value, was 1.22.

The properties of the resulting spherical activated carbon are listed in Tables 1 and 2.

Test 1 for Confirming Pharmacological Effects: Function to Improve a Renal Disease Renal failure model rats induced by subtotal nephrectomy of ¾ kidney were used to carry out a test for confirming

TABLE 1

| | | SSA | | Hg pore volume | | Average particle diameter |
|---|---|---|---|---|---|---|
| | Raw material | Langmuir $m^2/g$ | BET $m^2/g$ | 20~1000 nm | 7.5~15000 nm | μm |
| Example 1 | Phenolic resin | 2390 | 1860 | 0.0185 | 0.04 | 300 |
| Example 2 | Phenolic resin | 2100 | 1720 | 0.0272 | 0.06 | 430 |
| Example 3 | Phenolic resin | 2100 | 1670 | 0.0142 | 0.04 | 280 |
| Example 4 | Phenolic resin | 1930 | 1560 | 0.0185 | 0.06 | 410 |
| Example 5 | Ion-exchange resin | 1630 | 1250 | 0.2437 | 0.42 | 350 |
| Comparative Example 1 | Pitch | 2050 | 1540 | 0.0750 | 0.11 | 350 |
| Comparative Example 2 | Pitch | 2100 | 1650 | 0.0850 | 0.15 | 350 |

The Hg pore volume in Table 1 was determined by a mercury press-injection method and corresponds to a volume of pores having a diameter of 20 to 1000 nm.

The SSA (BET) in Table 1 is a found value of a specific surface area listed as a reference, and determined by the following method.

As the method for determination of a specific surface area by Langmuir's adsorption equation, nitrogen is adsorbed to the spherical activated carbon sample or the surface-modified spherical activated carbon sample at −196° C., and a relation of a nitrogen partial pressure and an adsorbed amount (absorption isotherm) is measured.

BET plotting is carried out, given that a relative pressure of nitrogen is p, and an adsorbed amount at that time is v ($cm^3/g$ STP). That is, the plotting in a range wherein p is 0.05 to 0.3 is carried out, in the field wherein a longitudinal axis is p/(v(1−p)), and an abscissa axis is p. From the gradient at that time of b (unit=$g/cm^3$), and an intercept of c (unit=$g/cm^3$), a specific surface area S (unit=$m^2/g$) can be calculated from the equation:

$$S = \frac{MA \times (6.02 \times 10^{23})}{22414 \times 10^{18} \times (b+c)}$$

wherein MA denotes a cross-sectional area of a nitrogen molecule, and was 0.162 $nm^2$.

pharmacological effects on a renal failure by an administration of the adsorbent for oral administration of the present invention. The adsorbents prepared in Examples 1 and 3 according to the present invention were used as a sample. After six weeks from the induction to produce model rats, the rats were divided into a control group (6 rats; hereinafter referred to as a C1 group), a group to which the adsorbent prepared in Example 1 was administered (6 rats; hereinafter referred to as a P1 group), and a group to which the adsorbent prepared in Example 3 was administered (6 rats; hereinafter referred to as a P2 group), so that there was no major imbalance therebetween.

A powdery feed was administered to the rats of the groups. An amount of the feed given to the rats of the groups was determined on the basis of an average amount of feed taken by the rats of the C1 group for 2 or 3 days. A mixed feed containing 5% by weight of the adsorbent for oral administration in the same powdery feed as that administered to the C1 group was administered to the rats of the P1 and P2 groups. After 8 weeks from the beginning of the administration of the adsorbents for oral administration, serum creatinine, urea-nitrogen, urinary creatinine, creatinine clearance, and an amount of protein excreted were measured. Further, a same test was carried out for six normal rats in which subtotal nephrectomy was not conducted (normal group).

Figure 7:
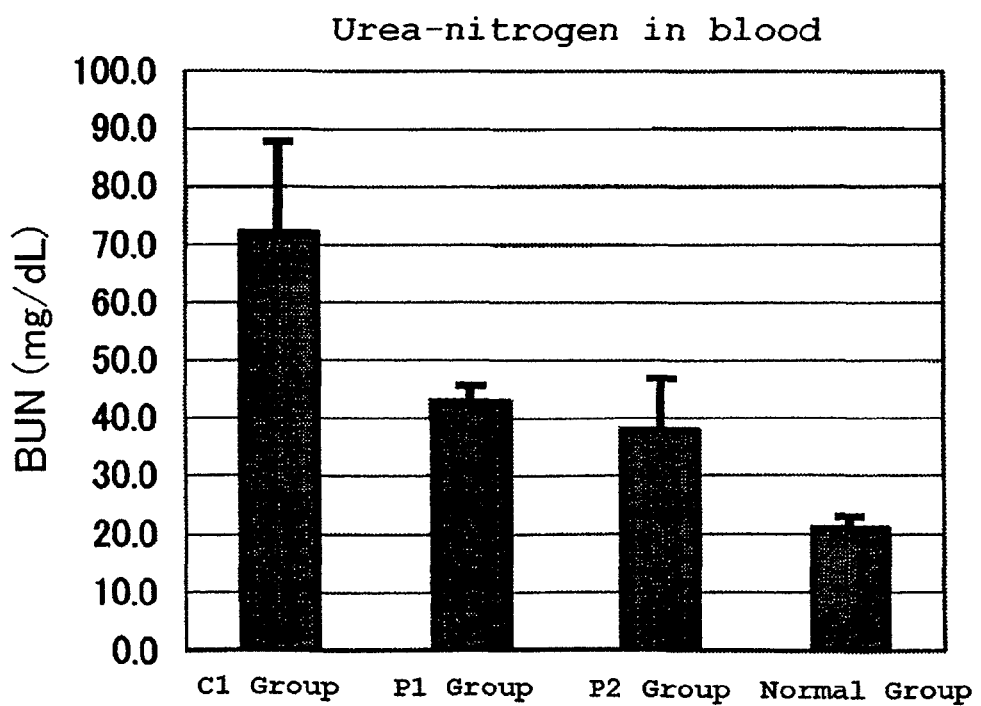
FIG. 7 is a graph showing the results of the investigation of the effect of the adsorbent for oral administration of the present invention on blood urea nitrogen.
Figure 8:
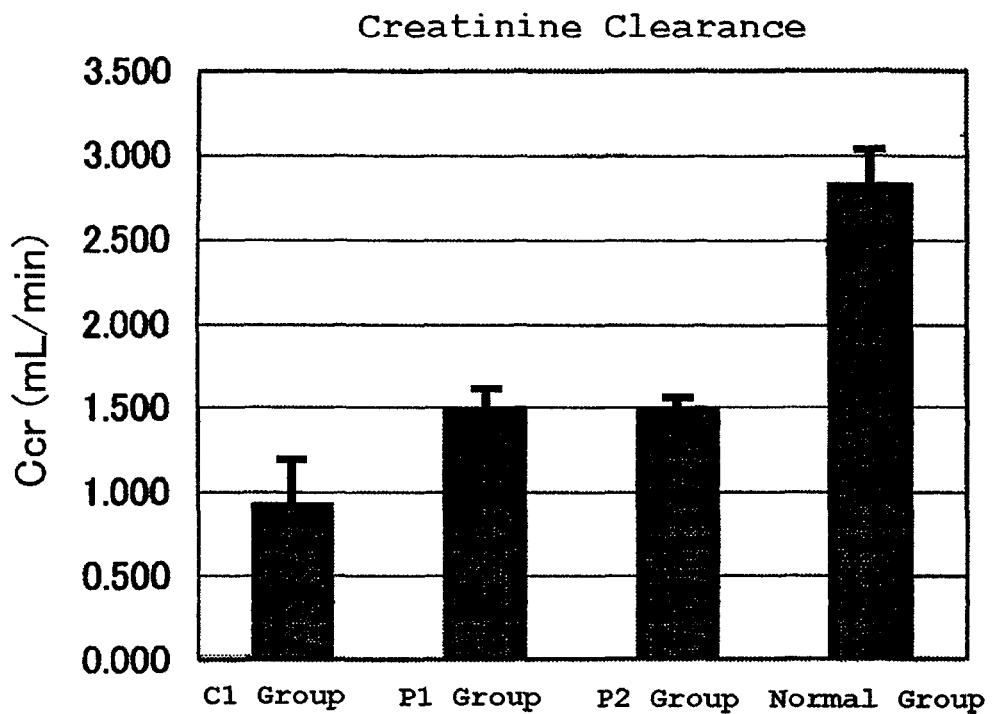
FIG. 8 is a graph showing the results of the investigation of the effect of the adsorbent for oral administration of the present invention on creatinine clearance.
Figure 9:
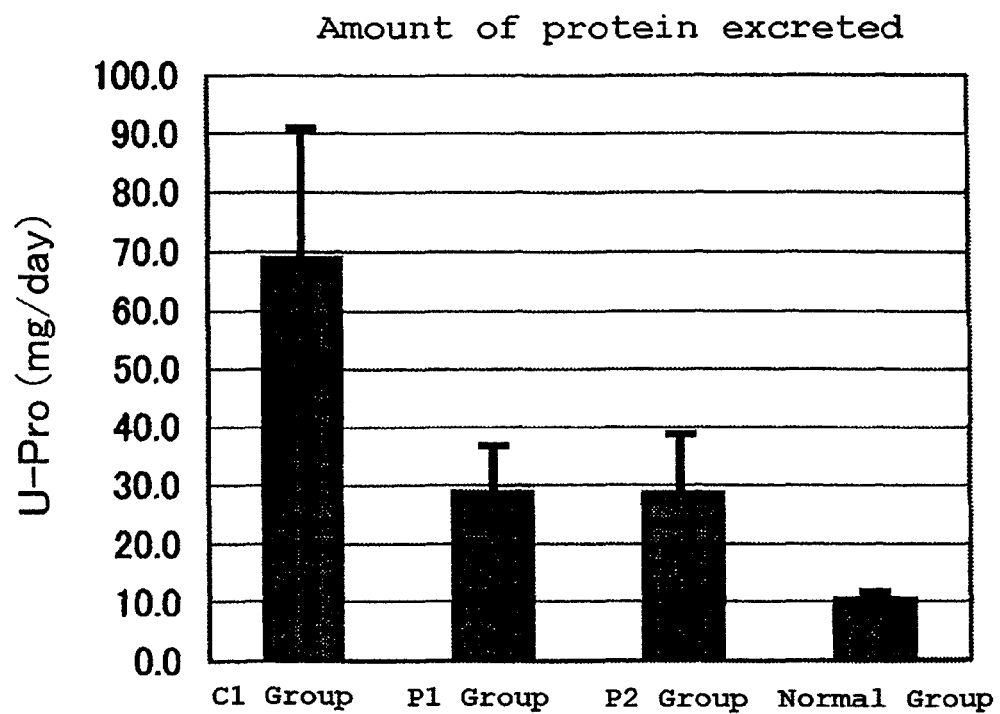
FIG. 9 is a graph showing the results of the investigation of the effect of the adsorbent for oral administration of the present invention on an amount of urine protein excreted.

The results are shown in FIGS. 6 to 9. In the P1 and P2 groups, serum creatinine (FIG. 6) and urea-nitrogen (FIG. 7)

TABLE 2

| | Total amount of acidic groups meq/g | Total amount of basic groups meq/g | Amount of α-amylase remaining in solutions (mg/dL) | | Amount of DL-β-aminoisobutyric acid remaining in solutions (mg/dL) | | Selective adsorbability | R Value |
|---|---|---|---|---|---|---|---|---|
| | | | 0.125 g | 0.50 g | 0.50 g | 2.50 g | | |
| Example 1 | 0.27 | 0.82 | 9.1 | 9.1 | 5.9 | 0.1 | 4.6 | 1.71 |
| Example 2 | 0.21 | 0.65 | 9.0 | 9.0 | 7.4 | 1.3 | 2.6 | 1.71 |
| Example 3 | 0.67 | 0.72 | 9.1 | 8.9 | 4.8 | 0.2 | 4.7 | 1.68 |
| Example 4 | 0.72 | 0.57 | 9.0 | 8.9 | 5.6 | 0.4 | 4.0 | 1.77 |
| Example 5 | 0.65 | 0.59 | 8.9 | 7.2 | 4.1 | 0.1 | 2.1 | 1.69 |
| Comparative Example 1 | 0.67 | 0.54 | 8.5 | 7.2 | 5.24 | 0.14 | 1.7 | 1.22 |
| Comparative Example 2 | 0.18 | 0.58 | 8.6 | 7.7 | 8.46 | 4.3 | 0.7 | 1.22 | were significantly lowered, respectively, in comparison with the C1 group, after 8 weeks from the beginning of the administration. As to creatinine clearance (FIG. 8), which is an index of a renal function, a reduction was recognized in the C1 group, whereas a significant inhibition of the reduction in the C1 group was observed in the P1 and P2 groups. Further, as to the amount of protein excreted (FIG. 9), an index of a function of a nephric tubules, an increase was recognized in the C1 group, whereas a significant inhibition of the increase in the C1 group was observed in the P1 and P2 groups. In addition, similar results were observed for urinary creatinine.

It is apparent from the above results that the adsorbent for oral administration of the present invention can inhibit a progress of a chronic renal failure, improve a chronic renal failure, prevent a renal hypofunction, or maintain a renal function.

Test 2 for Confirming Pharmacological Effects: Function to Improve a Liver Disease Hepatitis model rats induced by carbon tetrachloride were used to carry out a test for confirming pharmacological effects on a liver disease by an administration of the adsorbent for oral administration of the present invention. The adsorbents prepared in Examples 1 and 3 according to the present invention were used as a sample.

More particularly, carbon tetrachloride was subcutaneously administered at an amount of 12 mg/kg twice a week to Sprague-Dauley rats (produced by Clea Japan, Inc.; male; 7 weeks old), continuously for about 4 months until the end of the test for confirming pharmacological effects. After two months from the beginning of the administration of carbon tetrachloride, a reduction of liver function was confirmed, and thus, the rats were divided into a control group (6 rats; hereinafter referred to as a C2 group), a group to which the adsorbent prepared in Example 1 was administered (6 rats; hereinafter referred to as a Q1 group), and a group to which the adsorbent prepared in Example 3 was administered (6 rats; hereinafter referred to as a Q2 group), so that there was no major imbalance therebetween with respect to pathosis.

A powdery feed was administered to the rats of the groups. An amount of the feed given to the rats of the groups was determined on the basis of an average amount of feed taken by the rats of the C2 group for 2 or 3 days. A mixed feed containing 5% by weight of the adsorbent for oral administration in the same powdery feed as that administered to the C2 group was administered to the rats of the Q1 and Q2 groups for 2 months after the division to the groups. Further, a same test was carried out for six normal rats to which carbon tetrachloride was not administered (normal group).

Figure 10:
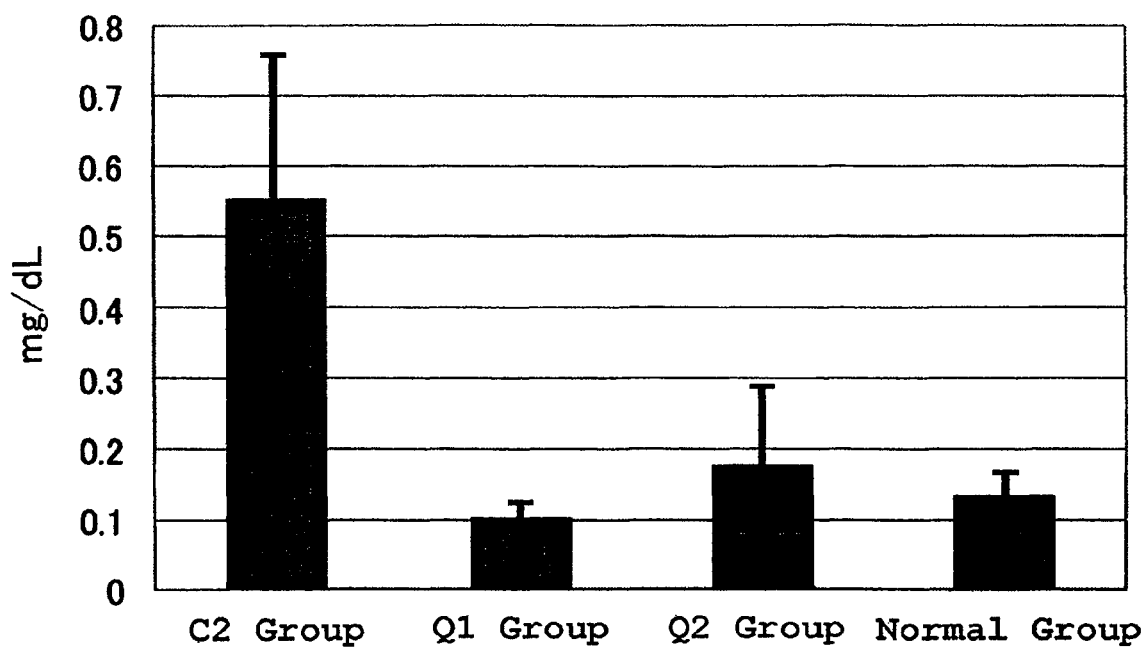
FIG. 10 is a graph showing the results of the investigation of the effect of the adsorbent for oral administration of the present invention on ICG (Indocyanine green).
Figure 11:
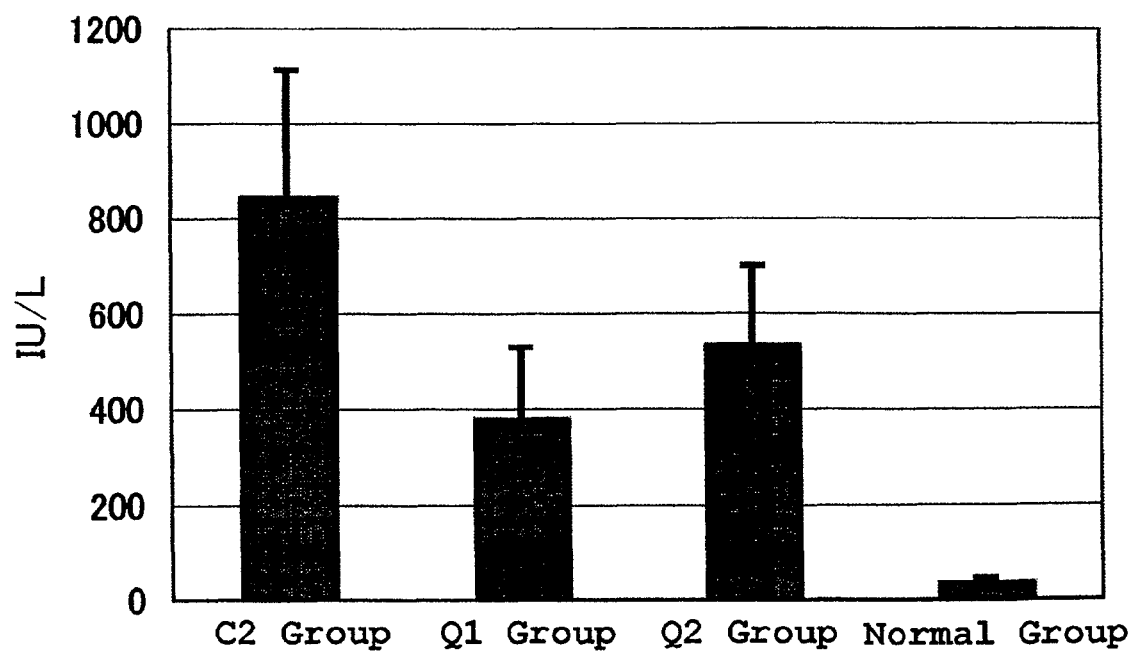
FIG. 11 is a graph showing the results of the investigation of the effect of the adsorbent for oral administration of the present invention on GOT (glutamic-oxaloacetic transaminase).
Figure 12:
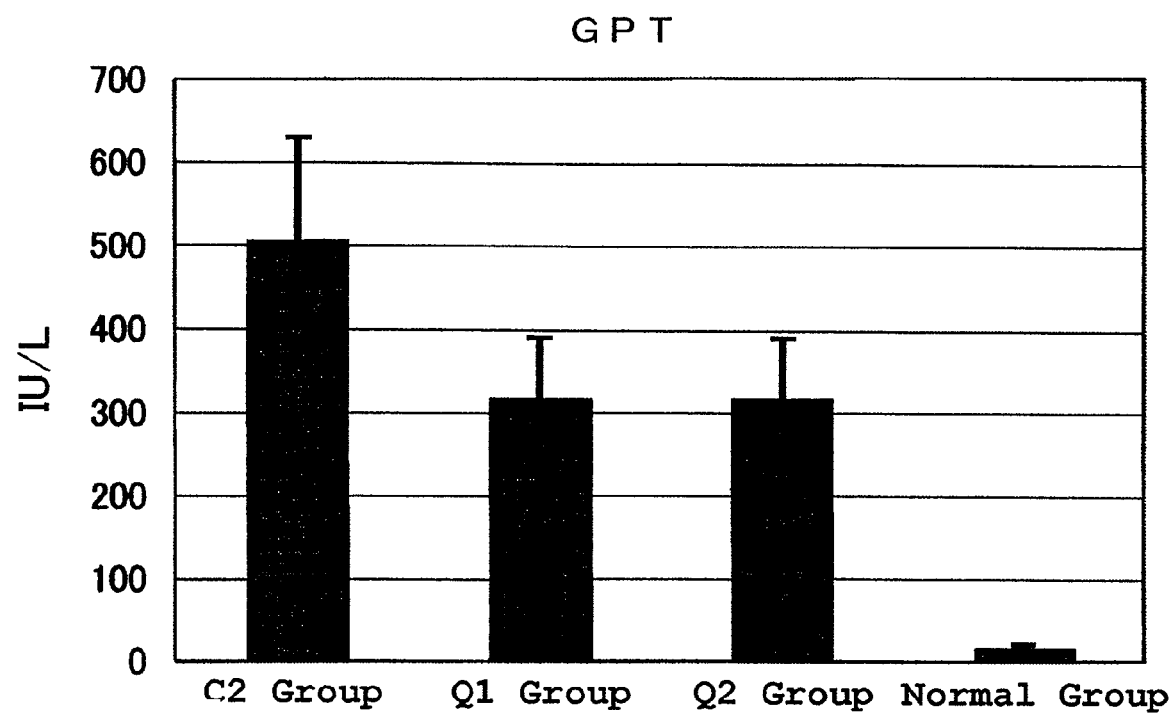
FIG. 12 is a graph showing the results of the investigation of the effect of the adsorbent for oral administration of the present invention on GPT (glutamic-pyruvic transaminase).

For about two months from the beginning of the administration of the adsorbent for oral administration to the end of the administration test, ICG (Indocyanine green), GOT (glutamic-oxaloacetic transaminase), and GPT (glutamic-pyruvic transaminase) were measured. The results obtained after two months from the beginning of the administration of the adsorbent for oral administration are shown in FIG. 10 (ICG), FIG. 11 (GOT), and FIG. 12 (GPT). Comparing the ICG test reflecting hepatic mesenchymal functions, the Q1 and Q2 groups showed significantly lower values than the C2 group. Further, the Q1 and Q2 groups showed significantly lower values than the C2 group, as to GOT and GPT which are leakage of cellular enzymes.

It is apparent from the above results that the adsorbent for oral administration of the present invention can improve a deterioration of liver functions.

Industrial Applicability

The adsorbent for oral administration according to the present invention has a specific pore structure, and thus, has an excellent selective adsorbability, that is, an excellent adsorbability of harmful toxins in an intestine, together with a low adsorbability of useful substances such as digestive enzymes or the like in a body, when orally administered, and the selective adsorbability is remarkably improved in comparison with that of the conventional adsorbent for oral administration.

The adsorbent for oral administration according to the present invention can be used as an adsorbent for oral administration for treating or preventing a renal disease, or an adsorbent for treating or preventing a liver disease.

As the renal disease, there may be mentioned, for example, chronic renal failure, acute renal failure, chronic pyelonephritis, acute pyelonephritis, chronic nephritis, acute nephritic syndrome, acute progressive nephritic syndrome, chronic nephritic syndrome, nephrotic syndrome, nephrosclerosis, interstitial nephritis, tubulopathy, lipoid nephrosis, diabetic nephropathy, renovascular hypertension, or hypertension syndrome, or secondary renal diseases caused by these primary diseases, or a light renal failure before a dialysis therapy, and may be used in an improvement of a light renal failure before a dialysis therapy or a disease condition for a patient during a dialysis therapy (see "Clinical Nephrology", Asakura-shoten, Nishio Honda, Kenkichi Koiso, and Kiyoshi Kurokawa, 1990; and "Nephrology" Igaku-shoin, Teruo Omae and Sei Fujimi, ed., 1981).

As the liver disease, there may be mentioned, for example, fulminant hepatitis, chronic hepatitis, viral hepatitis, alcoholic hepatitis, hepatic fibrosis, liver cirrhosis, hepatic cancer, autoimmune hepatitis, drug allergic hepatopathy, primary biliary cirrhosis, tremor, encephalopathia, dysbolism, or dysfunction. Further, the porous spherical carbonaceous substance can be used in a treatment of a disease caused by toxic substances in a body, such as psychosis.

Although the present invention has been described with reference to specific embodiments, various changes and modifications obvious to those skilled in the art are possible without departing from the scope of the appended claims.

The invention claimed is:

1. A pharmaceutical composition, comprising an adsorbent for oral administration and a pharmaceutically acceptable carrier or diluent, said adsorbent comprising a spherical activated carbon, wherein a diameter is 0.01 to 1 mm, a specific surface area determined by Langmuir's adsorption equation is 1000 m$^2$/g or more, and a diffraction intensity ratio, an R value, determined by an equation (1):

$$R=(I_{15}-I_{35})/(I_{24}-I_{35}) \quad (1)$$

wherein $I_{15}$ is a diffraction intensity when a diffraction angle (2θ) of an X-ray diffractometry is 15°, $I_{35}$ is a diffraction intensity when a diffraction angle (2θ) of an X-ray diffractometry is 35°, and $I_{24}$ is a diffraction intensity when a diffraction angle (2θ) of an X-ray diffractometry is 24°, is 1.4 or more.

2. The pharmaceutical composition according to claim 1, wherein a volume of pores having a diameter of 20 to 1000 nm is 1 mL/g or less.

3. The pharmaceutical composition according to claim 1, wherein a volume of pores having a diameter of 7.5 to 15000 nm is less than 0.25 mL/g.

4. The pharmaceutical composition according to claim 1, wherein the spherical activated carbon is prepared from the thermosetting resin, as a carbon source.

5. The pharmaceutical composition according to claim 1, wherein the spherical activated carbon is prepared from the thermosetting resin having a carbonization yield of 40% by weight or more by a heat-treatment at 800° C. in an atmosphere of non-oxidative gas, as a carbon source.

6. A pharmaceutical composition, comprising an adsorbent for oral administration and a pharmaceutically acceptable carrier or diluent, said adsorbent comprising a surface-modified spherical activated carbon, wherein a diameter is 0.01 to 1 mm, a specific surface area determined by Langmuir's adsorption equation is 1000 m²/g or more, a total amount of acidic groups is 0.40 to 1.00 meq/g, a total amount of basic groups is 0.40 to 1.10 meq/g, and a diffraction intensity ratio, an R value, determined by an equation (1):

$$R=(I_{15}-I_{35})/(I_{24}-I_{35}) \quad (1)$$

wherein $I_{15}$ is a diffraction intensity when a diffraction angle (2θ) of an X-ray diffractometry is 15°, $I_{35}$ is a diffraction intensity when a diffraction angle (2θ) of an X-ray diffractometry is 35°, and $I_{24}$ is a diffraction intensity when a diffraction angle (2θ) of an X-ray diffractometry is 24°, is 1.4 or more.

7. The pharmaceutical composition according to claim 6, wherein a volume or pores having a diameter of 20 to 1000 nm is 1 mL/g or less.

8. The pharmaceutical composition according to claim 6, wherein a volume of pores having a diameter of 7.5 to 15000 nm is less than 0.25 mL/g.

9. The pharmaceutical composition according to claim 6, wherein the spherical activated carbon is prepared from a thermosetting resin, as a carbon source.

10. The pharmaceutical composition according to claim 6, wherein the surface-modified spherical activated carbon is prepared from the thermosetting resin having a carbonization yield of 40% by weight or more by a heat-treatment at 800° C. in an atmosphere of non-oxidative gas, as a carbon source.

11. A method for treating or preventing a renal disease, comprising orally administering to a subject in need thereof an effective amount of the pharmaceutical composition of claim 1.

12. A method for treating or preventing a renal disease, comprising orally administering to a subject in need thereof an effective amount of the pharmaceutical composition of claim 6.

13. A method for treating or preventing a liver disease, comprising orally administering to a subject in need thereof an effective amount of the pharmaceutical composition of claim 1.

14. A method for treating or preventing a liver disease, comprising orally administering to a subject in need thereof an effective amount of the pharmaceutical composition of claim 6.

* * * * *